United States Patent [19]
Florio

[11] 4,277,847
[45] Jul. 14, 1981

[54] HEADBAND FOR JOGGERS

[75] Inventor: John D. Florio, Miami, Fla.

[73] Assignee: Jose Estrada, Miami, Fla.

[21] Appl. No.: 136,294

[22] Filed: Apr. 1, 1980

[51] Int. Cl.$^3$ .............................................. A42B 1/24
[52] U.S. Cl. ........................................... 2/12; 2/171;
2/199; 2/DIG. 11
[58] Field of Search ................... 2/171, 171.1, 185 R,
2/199, 12, 422, DIG. 11, 207

[56] References Cited
U.S. PATENT DOCUMENTS

| 765,730 | 7/1904 | Hoag | 2/185 R |
| 792,533 | 6/1905 | Miller | 2/185 R X |
| 1,626,433 | 4/1927 | Siner | 2/DIG. 11 |
| 3,765,031 | 10/1973 | Beresic | 2/422 X |
| 4,179,753 | 12/1979 | Aronberg et al. | 2/422 X |

FOREIGN PATENT DOCUMENTS

| 2390116 | 12/1978 | France | 2/DIG. 11 |
| 462984 | 4/1951 | Italy | 2/171 |

Primary Examiner—Peter P. Nerbun
Attorney, Agent, or Firm—Harvey B. Jacobson

[57] ABSTRACT

A water absorbent material such as terry cloth is cut into a rectangle. A smaller rectangle of nylon or other water repellent material is sewn over one portion of the terry cloth and that portion is folded over onto itself and sewn together to form watertight pockets. A flap remains which covers the pockets. A hook-type fastener such as is sold under the name "Velcro" is used to hold the flap in a covering position and additional "Velcro" is contained on the ends of the terry cloth to hold the ends together about a user's head. Optionally, a visor may be sewn onto the headband.

6 Claims, 6 Drawing Figures

HEADBAND FOR JOGGERS

BACKGROUND OF THE INVENTION

1. Field of the Invention

This invention relates to headwear and especially to headwear in the form of moisture absorbing bands for inhibiting the flow of perspiration from a user's forehead.

2. Discussion of Related Art

It has been known for a long time to use absorbent material wrapped around one's head to absorb perspiration during vigorous physical exercise. During certain forms of exercise, especially jogging, one finds it desirable to have additional areas of storage on one's body which can be used for storing items such as paper money which should be kept in a clean, dry condition.

Examples of known headband-type devices include that shown in U.S. Pat. No. 1,434,854, issued Nov. 7, 1922 to Stall. The Stall device comprises an elongated absorbent pad adapted to conform closely to the forehead. A flexible casing encloses the pad and has a portion formed of absorbent material that contacts with the wearer's forehead. The pad and casing constitute a front section adapted to contact throughout the area of its inner face with the forehead. U.S. Pat. No. 1,697,919, issued Jan. 8, 1919 to Knepper, shows a perspiration pad which comprises a flexible body composed of an absorbent filler enclosed in a gauze cover. The cover is wrapped around the filler with its longitudinal ends overlapped and its ends folded back along the sides of the body. A pair of spring clips are attachably clamped on the ends of the pad body and an elastic strap is stretched between the spring clips to hold the pad against the user's head. U.S. Pat. No. 1,897.146, issued Feb. 14, 1933 to Richardson, shows a headband which comprises a single strip of elastic material having an elongated straight middle portion and two curved end portions. The extremities of the curved portions are reduced to form tabs with a male member of a snap fastener on one tab and a female member of the snap fastener being disposed on the other tab.

SUMMARY OF THE INVENTION

One object of the present invention is to provide a headband which incorporates waterproof pouches for storing paper money and other items which must be kept dry.

A further object of the present invention is to provide a headband which can be manufactured relatively inexpensively, yet is easy to use and functions well for its intended purpose.

Another object of the present invention is to provide a headband which is lightweight, completely washable and can be manufactured in one size to fit all average head sizes.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
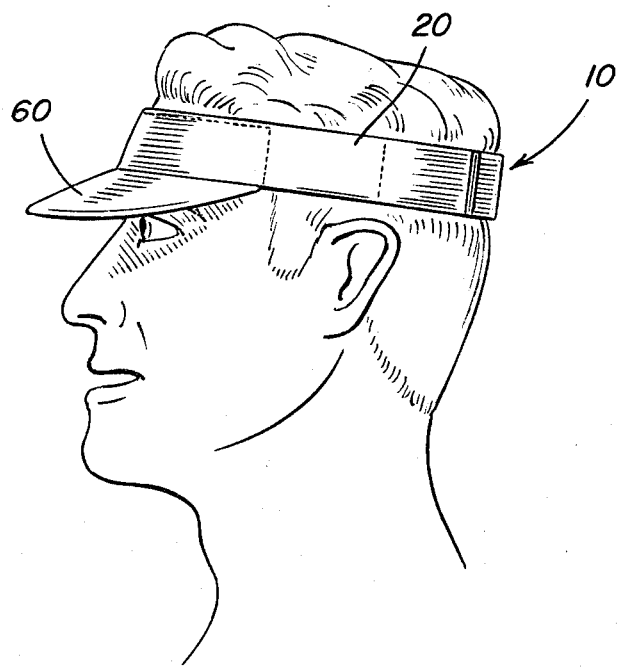
FIG. 1 is a side elevational view of the headband shown in place on a user's head.
Figure 2:
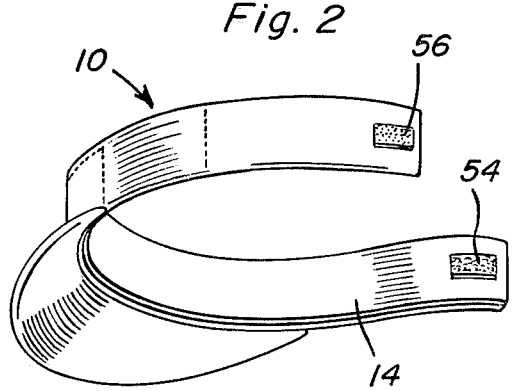
FIG. 2 is a perspective view of the headband.
Figure 5:
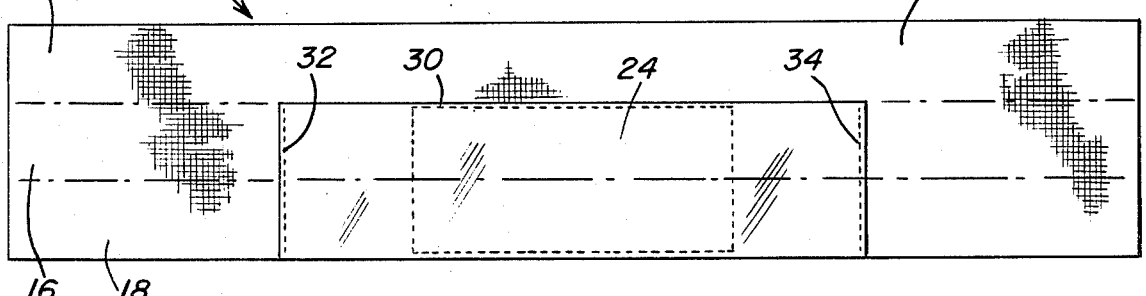
FIG. 5 is a top elevational view showing the headband in its first stage of formation.
Figure 6:
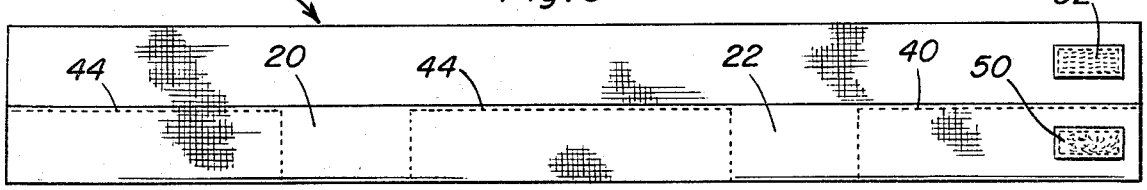
FIG. 6 is a top elevational view of the headband shown with the flap completely open.

Now with reference to the drawings, a headband incorporating the principles and concepts of the present invention and generally referred to by the reference numeral 10 will be described in detail. It can be seen that headband 10 comprises a substantially rectangular piece of absorbent material such as terry cloth labelled with the reference numeral 12. Terry cloth piece 12 is divided into three longitudinally extending sections 14, 16 and 18. Sections 16 and 18 comprise the body of the headband while section 14 comprises the flap which is used to cover the body. A pair of pockets 20 and 22 are formed in the headband by placing a smaller substantially rectangular piece of water resistant material such as nylon, generally referred to by the reference numeral 24, in the longitudinal center of sections 16 and 18. In practice, the terry cloth 12 can be approximately 26 inches long by 5-¼ inches in width with the nylon material being 13-½ inches long and 3-½ inches wide. The nylon material is laid on the terry cloth as shown in FIG. 5 and can be stitched in place, as indicated by stitch lines 30, 32 and 34 if desired. With or without stitching, with the nylon material 24 in place the lower section 18 is folded up onto section 16 so that the material 24 is folded onto itself forming pockets 20 and 22. The folded sections 16 and 18 are sewn along stitch lines 40, 42 and 44 as shown in FIG. 6 leaving the tops of pockets 20 and 22 open with the pockets being lined with nylon material 24. Obviously, the actual dimensions of the pockets 20, 22 can vary as desired by selective placement of stitch lines 40, 42, and 44. Once the stitching has been done, a pair of cooperating "Velcro" pads 50 and 52 are attached to the inside of flap 14 and the outside of section 18 as shown in FIG. 6 in order to hold the flap down over section 18 thus covering pockets 20 and 22. Additional cooperating "Velcro" pads 54 and 56 are attached to the outside of flap 14 and the outside of section 18 as shown in FIG. 2 in order to hold the ends of the headband together when in place about a user's head as depicted in FIG. 1. By use of "Velcro" pads 54, 56, a degree of adjustability for the headband can be had by simply overlapping the pads to provide a firm fit to the head of the user. Access to the pockets 20, 22 can easily be had by simply removing the headband and pulling "Velcro" pads 50, 52 apart thereby lifting flap 14 to expose the desired pocket.

Figure 3:
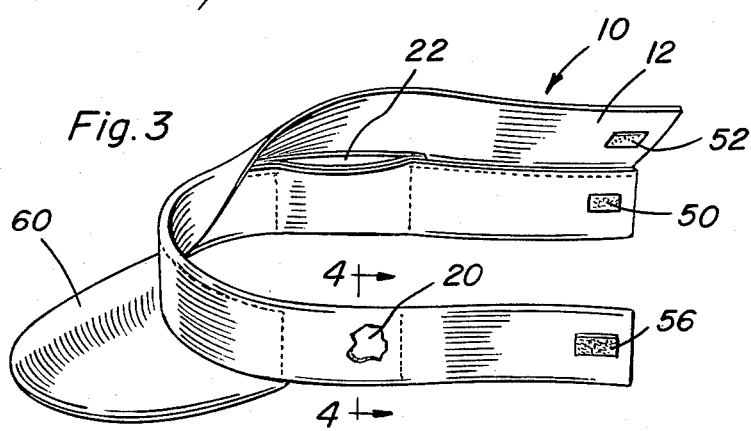
FIG. 3 is a perspective view of the headband showing the covering flap partially open to expose one of the pockets.
Figure 4:
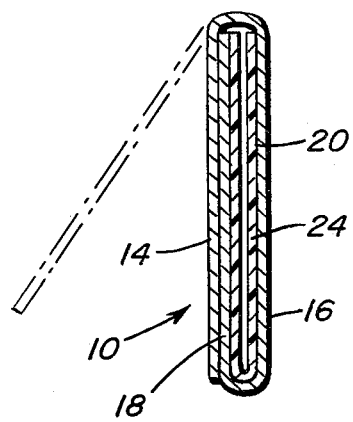
FIG. 4 is an elevational section view taken substantially along a plane passing through section line 4—4 of FIG. 3.

Additionally, a visor 60 can be attached as a permanent part of the headband by simply sewing it to the bottom edge of the formed headband as shown in FIG. 3. Visor 60 is merely an option which can be added if desired and is a permanent part of the headband when added.

Accordingly, headband 10 contains pockets 20 and 22 which are built into the headband directly with the headband being part of the standard jogging uniform. Thus pockets are available to the user at all times. The entire headband is lightweight, completely washable and can be adjusted to fit all average sized heads. The pockets 20, 22 can be used to carry keys, coins, cash, I.D. cards, paper money, etc. When the flap 14 is folded over the pockets and the band is wrapped about the user's head, the pockets 20 and 22 fit on the side of the user's head in the temporal area and provide a secure position from which the items disposed in the pocket cannot be easily lost or jostled free.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A headband for use in sporting events comprising an elongated piece of absorbent material divided into three longitudinally extending sections, a smaller piece of elongated water resistant material covering a portion of two adjacent longitudinally extending sections, wherein said two adjacent longitudinally extending sections are folded one over the other and sewn together to form pockets with said water resistant material comprising the inner lining of said pockets with the remaining longitudinally extending section being foldable over said pockets to provide a cover therefor.

2. The invention as defined in claim 1 and further including cooperating attachment element connected to facing portions of said flap and said folded two adjacent longitudinally extending sections for holding said flap over said pockets.

3. The invention as defined in claim 2 wherein said attachment elements comprise hook and pile fastener pads.

4. The invention as defined in claim 3 and further including additional cooperating attachment elements, one of said additional attachment elements being connected to an outward facing side of said two adjacent folded sections, the other of said additional attachment elements being connected to a facing portion of said cover opposite from the position of said first mentioned attachment element connected to said cover.

5. The invention as defined in claim 1 and further including a visor fixedly attached at a fold between said two adjacent folded elements.

6. The invention as defined in claim 1 wherein said pockets are disposed one on each side of a center portion of said headband for overlying lateral portions of a user's head.

* * * * *